(12) United States Patent
Lim et al.

(10) Patent No.: US 8,202,257 B2
(45) Date of Patent: Jun. 19, 2012

(54) SPLATTER PREVENTION MECHANISM FOR A SYRINGE

(75) Inventors: Kiang Heng Lim, Singapore (SG); Steven Choon Meng Lau, Singapore (SG); Jon Yao Han Moh, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1310 days.

(21) Appl. No.: 11/240,614

(22) Filed: Sep. 30, 2005

(65) Prior Publication Data

US 2006/0195063 A1 Aug. 31, 2006

Related U.S. Application Data

(63) Continuation-in-part of application No. 10/835,848, filed on Apr. 30, 2004, now abandoned, and a continuation-in-part of application No. 11/196,699, filed on Aug. 3, 2005, now Pat. No. 7,798,993, which is a continuation of application No. 10/256,607, filed on Sep. 27, 2002, now abandoned, and a continuation-in-part of application No. 10/706,795, filed on Nov. 12, 2003, now abandoned, which is a continuation of application No. 09/941,030, filed on Aug. 28, 2001, now abandoned, which is a continuation-in-part of application No. 09/274,117, filed on Mar. 23, 1999, now Pat. No. 6,361,525, which is a continuation-in-part of application No. 09/249,431, filed on Feb. 12, 1999, now abandoned, which is a continuation-in-part of application No. 09/124,447, filed on Jul. 29, 1998, now abandoned.

(51) Int. Cl.
*A61M 5/315* (2006.01)

(52) U.S. Cl. ........................................ 604/218; 604/221

(58) Field of Classification Search ................... 604/181, 604/187, 218–231, 110, 82–92
See application file for complete search history.

(56) References Cited

U.S. PATENT DOCUMENTS 1,742,497 A 1/1930 Dickinson
(Continued)

FOREIGN PATENT DOCUMENTS

DE 2939180 4/1980
(Continued)

OTHER PUBLICATIONS

PCT International Search Report in PCT/US2006/030076, (Feb. 5, 2008), 7 pgs.

(Continued)

*Primary Examiner* — Kevin C Sirmons
*Assistant Examiner* — Phillip Gray
(74) *Attorney, Agent, or Firm* — Jeanne P. Lukasavage; Diehl Servilla LLC

(57) ABSTRACT

A syringe including a barrel and a plunger slidably disposed within the barrel is disclosed. A distal end of the barrel defines a roof, and an elongate tip, in fluid communication with the barrel, extends from the roof. A protrusion forming a ridge may be disposed on one of the roof of the barrel and the plunger head. When the plunger head contacts the roof, the protrusion forms a channel between the plunger head and the roof. The channel isolates fluid within the channel from the elongate tip, which in turn reduces the spray of fluid through the distal end of the syringe. In another embodiment to reduce the spray of fluid through the distal end of the syringe, an impulse reduction system may be used to reduce or prevent the proximal portion from applying a distally directed impulse to the distal portion after the breakable connection is broken.

11 Claims, 20 Drawing Sheets

U.S. PATENT DOCUMENTS

| | | |
|---|---|---|
| 1,793,068 A | 2/1931 | Dickinson |
| 2,158,593 A | 5/1939 | Scrimgeour |
| 2,902,995 A | 9/1959 | Loper |
| 3,179,107 A | 4/1965 | Clark |
| 3,234,944 A | 2/1966 | Stevens et al. |
| 3,301,256 A | 1/1967 | Cowley |
| 3,320,954 A | 5/1967 | Cowley |
| 3,331,538 A | 7/1967 | Higgins |
| 3,469,581 A | 9/1969 | Burke |
| 3,491,757 A | 1/1970 | Arce |
| 3,542,024 A | 11/1970 | Burke |
| 3,712,302 A | 1/1973 | Burke et al. |
| 4,022,191 A | 5/1977 | Jamshidi |
| 4,027,669 A | 6/1977 | Johnston et al. |
| 4,215,701 A * | 8/1980 | Raitto .......... 600/576 |
| 4,245,654 A | 1/1981 | Raitto |
| 4,430,080 A | 2/1984 | Pasquini et al. |
| 4,676,530 A | 6/1987 | Nordgren et al. |
| 4,699,614 A | 10/1987 | Glazier |
| 4,720,285 A | 1/1988 | Pickhard |
| 4,775,363 A | 10/1988 | Sandsdalen |
| 4,775,364 A | 10/1988 | Alles |
| 4,787,891 A | 11/1988 | Levin et al. |
| 4,863,427 A | 9/1989 | Cocchi |
| 4,874,384 A | 10/1989 | Nunez |
| 4,883,466 A | 11/1989 | Glazier |
| 4,915,692 A | 4/1990 | Verlier |
| 4,923,443 A | 5/1990 | Greenwood et al. |
| 4,950,240 A | 8/1990 | Greenwood et al. |
| 4,973,308 A | 11/1990 | Borras et al. |
| 4,973,309 A | 11/1990 | Sultan |
| 5,000,735 A | 3/1991 | Whelan |
| 5,004,460 A | 4/1991 | Gimeno |
| 5,047,017 A | 9/1991 | Koska |
| 5,059,172 A | 10/1991 | Sutherland et al. |
| 5,067,942 A | 11/1991 | Jaffee et al. |
| 5,069,225 A | 12/1991 | Okamura |
| 5,078,686 A | 1/1992 | Bates |
| 5,085,638 A | 2/1992 | Farbstein et al. |
| 5,149,323 A | 9/1992 | Colonna |
| 5,158,550 A | 10/1992 | Scholl, Jr. |
| 5,163,908 A | 11/1992 | Lambert |
| 5,181,912 A | 1/1993 | Hammet |
| 5,201,709 A | 4/1993 | Capra |
| 5,205,833 A | 4/1993 | Harsh et al. |
| 5,215,524 A | 6/1993 | Vallelunga et al. |
| 5,221,267 A | 6/1993 | Folden |
| 5,226,882 A | 7/1993 | Bates |
| 5,242,401 A | 9/1993 | Colsky |
| 5,248,299 A | 9/1993 | Ota |
| 5,269,760 A * | 12/1993 | Bina .......... 604/110 |
| 5,336,200 A | 8/1994 | Streck et al. |
| 5,344,405 A | 9/1994 | Richards |
| 5,352,203 A | 10/1994 | Vallelunga et al. |
| 5,383,857 A | 1/1995 | Levitov |
| 5,389,075 A | 2/1995 | Vladimirsky |
| 5,423,756 A | 6/1995 | van der Merwe |
| 5,489,272 A | 2/1996 | Wirtz |
| 5,527,286 A | 6/1996 | Lekhgolts et al. |
| 5,605,544 A | 2/1997 | Tsao |
| 5,643,211 A | 7/1997 | Sadowski et al. |
| 5,697,917 A | 12/1997 | Sadowski et al. |
| 5,738,655 A | 4/1998 | Vallelunga et al. |
| 5,769,822 A | 6/1998 | McGary et al. |
| 5,795,337 A | 8/1998 | Grimard |
| 5,807,374 A | 9/1998 | Caizza et al. |
| 5,833,660 A | 11/1998 | Nathan et al. |
| 5,836,919 A | 11/1998 | Skurka et al. |
| 5,919,169 A | 7/1999 | Grams et al. |
| 5,928,202 A | 7/1999 | Linnebjerg |
| 5,989,219 A | 11/1999 | Villas et al. |
| 6,013,056 A | 1/2000 | Pettersen |
| 6,017,325 A | 1/2000 | Yerfino et al. |
| 6,053,892 A | 4/2000 | Meyer |
| 6,120,479 A | 9/2000 | Campbell et al. |
| 6,139,526 A | 10/2000 | Bedner et al. |
| 6,217,550 B1 | 4/2001 | Capes |
| 6,251,095 B1 | 6/2001 | Liu |
| 6,267,749 B1 | 7/2001 | Miklos et al. |
| 6,361,525 B2 | 3/2002 | Capes et al. |
| 6,607,507 B2 | 8/2003 | Schottli |
| 7,534,233 B2 * | 5/2009 | Schiller et al. .......... 604/218 |
| 2002/0107489 A1 | 8/2002 | Lee |
| 2004/0010235 A1 | 1/2004 | Weilbacher et al. |
| 2004/0097884 A1 | 5/2004 | Capes et al. |
| 2004/0199113 A1 | 10/2004 | Capes et al. |
| 2005/0154353 A1 | 7/2005 | Alheidt |
| 2006/0195063 A1 | 8/2006 | Lim et al. |

FOREIGN PATENT DOCUMENTS

| | | |
|---|---|---|
| DE | 10159696 | 6/2003 |
| EP | 0364777 | 4/1990 |
| EP | 0412968 | 2/1991 |
| EP | 030804 | 4/1994 |
| FR | 2720649 | 12/1995 |
| GB | 1286690 | 8/1972 |
| GB | 2214082 | 8/1989 |
| GB | 2256146 | 12/1992 |
| GB | 2318060 | 4/1998 |
| WO | WO-90/03816 | 4/1990 |
| WO | WO-95/23005 | 8/1995 |
| WO | WO-96/30076 | 10/1996 |
| WO | WO-97/31665 | 9/1997 |
| WO | WO-97/41903 | 11/1997 |
| WO | WO-98/02198 | 1/1998 |
| WO | WO-99/52578 | 10/1999 |
| WO | WO-00/59564 | 10/2000 |
| WO | WO-01/62319 | 8/2001 |
| WO | WO-01/80930 | 11/2001 |
| WO | WO-02/070053 | 9/2002 |
| WO | WO-2004/033006 | 4/2004 |
| WO | WO-2004/033018 | 4/2004 |
| WO | WO-2004/078243 | 9/2004 |
| WO | WO-2005/032626 | 4/2005 |
| WO | WO-2005/032628 | 4/2005 |
| WO | WO-2005/061030 | 7/2005 |

OTHER PUBLICATIONS

PCT Written Opinion in PCT/US2006/030076, (Feb. 5, 2008), 6 pgs.

PCT International Search Report in PCT/US2006/030050, (Feb. 5, 2008), 7 pgs.

PCT Written Opinion in PCT/US2006/030050, (Feb. 5, 2008), 6 pgs.

* cited by examiner

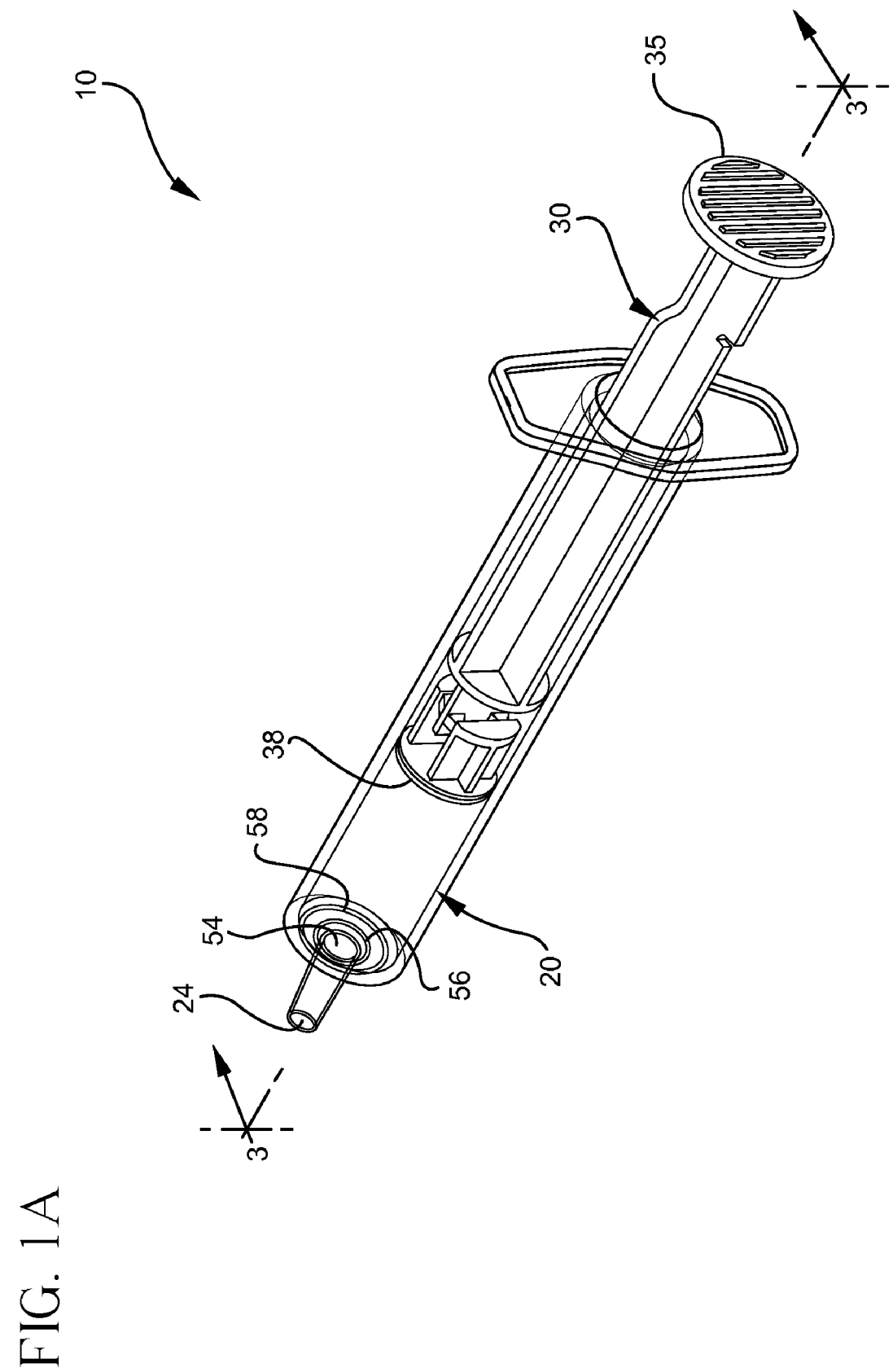

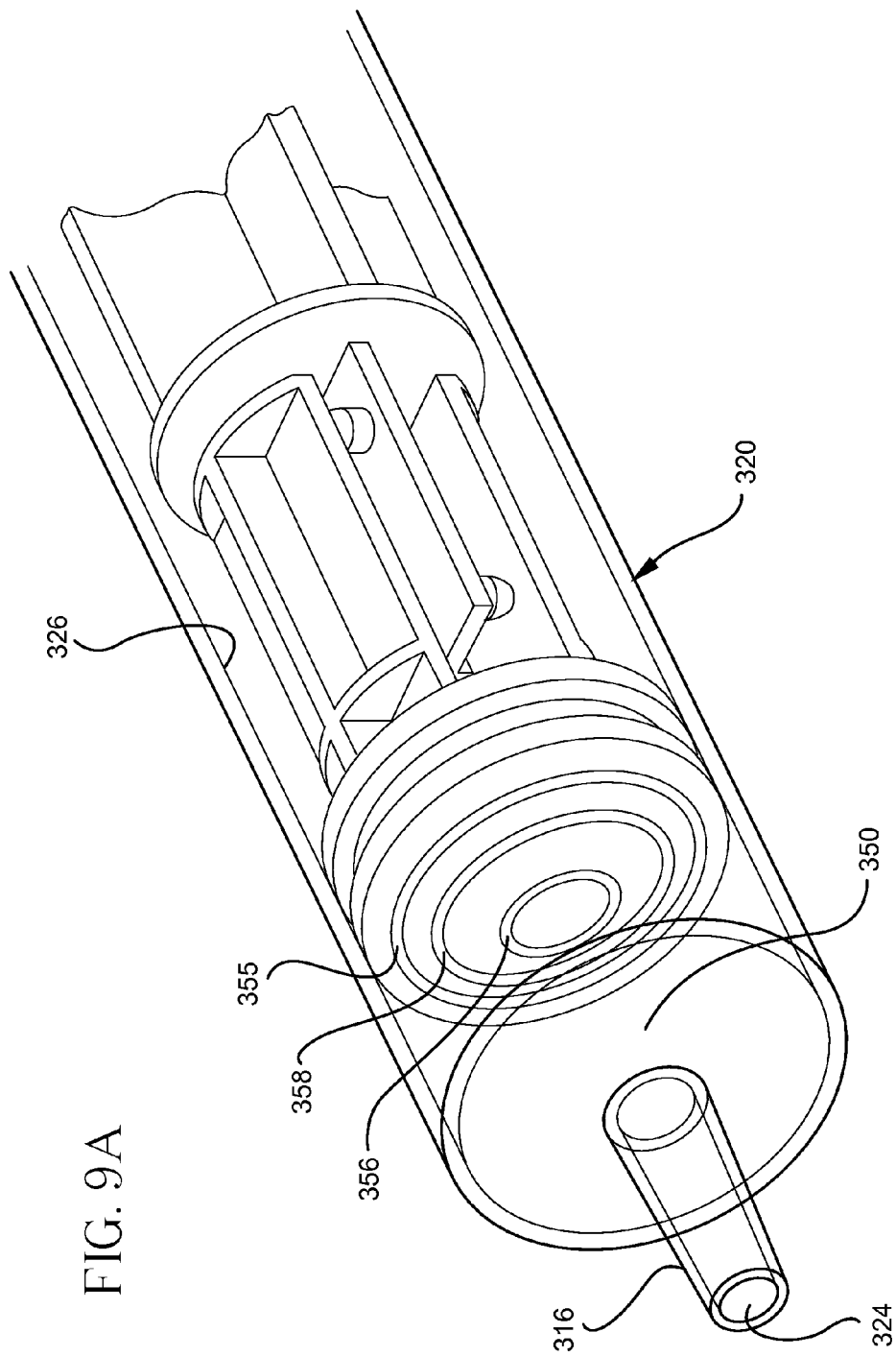

SPLATTER PREVENTION MECHANISM FOR A SYRINGE

CROSS-REFERENCE TO RELATED APPLICATIONS

This application is a continuation-in-part of U.S. application Ser. No. 10/835,848, filed Apr. 30, 2004 and U.S. application Ser. No. 11/196,699, filed Aug. 3, 2005, which is a continuation-in-part of application Ser. No. 10/835,848, filed Apr. 30, 2005, which is a continuation of U.S. patent application Ser. No. 10/256,607 filed Sep. 27, 2002 and a continuation-in-part of U.S. patent application Ser. No. 10/706,795 filed Nov. 12, 2003, which is a continuation of U.S. patent application Ser. No. 09/941,030 filed Aug. 28, 2001 now abandoned, which is a continuation-in-part of U.S. patent application Ser. No. 09/274,117 filed May 14, 2001, now U.S. Pat. No. 6,361,525, which is a continuation-in-part of U.S. patent application Ser. No. 09/249,431 filed on Feb. 12, 1999, now abandoned, which is a continuation-in-part of U.S. application Ser. No. 09/124,447 filed Jul. 28, 1998, now abandoned. The content of each of these applications is incorporated by reference.

BACKGROUND OF THE INVENTION

The present invention relates to a syringe that reduces spray of fluid from the end of a syringe and the needle mounted to the end of the syringe.

Throughout the world, the re-use of hypodermic syringe products, which are intended for single-use only, is a problem which causes the transfer of contagious diseases. Intravenous drug users who routinely share and re-use syringes are a high-risk group with respect to the AIDS virus. Also, the effects of multiple syringe use are a major concern in some countries where the repeated use of syringe products during mass inoculation programs may be responsible for the spread of many diseases. Syringes are often recycled in developing countries without proper sterilization.

To alleviate these problems, syringes have been designed with collapsible plunger rods which render the syringe effectively unusable after its intended use. For example, as disclosed in U.S. Pat. No. 6,217,550 (Capes et. al), the entire content of which is incorporated herein by reference, the plunger rod is provided weak points so that when pressed with excessive force at the completion of an injection, the plunger breaks into two unusable parts. Thus, the user expels as much fluid as possible from the barrel of the syringe as would normally be done, and then presses hard upon the plunger thumb press to break the plunger rod. Syringes of this type, which are capable of being used only once, will be referred to herein as single use syringes.

In single use syringes, when the user breaks the plunger rod, the proximal part of the plunger rod moves forward at high speed into the distal part of the plunger rod. The collision between these parts creates an impulse that compresses the plunger, and which thus compresses whatever fluid may remain in the dead space between the plunger and roof of the barrel. This results in a spray of fluid from the nozzle of the syringe. As used herein, the nozzle of the syringe refers to the opening at the distal end of the syringe and/or the hollow needle located at the distal end of the syringe. The spray of fluid from the nozzle of a syringe may also be problematic in traditional syringes as well when a user presses on the thumb press of the plunger rod with excessive force. Such spraying poses a risk of spreading contaminated fluids, such as contaminated fluid blood. It would therefore be desirable to provide syringes, mechanisms and methods that reduce the spray from the nozzle of syringes, and in particular single use syringes.

SUMMARY OF THE INVENTION

In one embodiment, a syringe comprises a barrel having a fluid chamber, a proximal end, a distal end defining a roof facing the proximal end, and an elongate tip extending from the distal end. The elongate tip has a passageway that is in fluid communication with the chamber. A plunger is slidably disposed within the barrel, the plunger having a plunger head that faces the roof. One or more protrusions are disposed on one or both of the plunger head and the roof. When the plunger head contacts the roof, the protrusion forms a reservoir or channel between the roof and the plunger head adapted to isolate fluid from the passageway. In other words, the reservoir or channel is not in fluid communication with the passageway. Hence, any fluid within the channel cannot be expelled through the passageway, and hence cannot spray out of the elongate tip.

In one embodiment, the protrusion forms a first closed ridge that is substantially concentric with the passageway when the plunger head is fully distally disposed within the barrel. In other embodiments, yet another protrusion, disposed on one of the plunger head and the roof, forms a second ridge. This second ridge may be a closed ridge that is substantially concentric with the first closed ridge, or that intercepts the first closed ridge. In another embodiment, the second ridge may extend in a substantially radial manner from the first closed ridge. In yet another embodiment, the protrusion or protrusions are formed integrally with the roof or plunger head.

In another embodiment, the syringe may further comprise a single use syringe. Such a single use syringe may include a breakable plunger rod. The single use syringe may further comprise an impulse reduction system. In one embodiment that includes a breakable plunger rod, the breakable plunger rod may comprise a proximal portion connected to a distal portion with a breakable connection. The distal portion includes the plunger, which is positioned in fluid-tight engagement with the inside surface of the chamber. The breakable connection is strong enough to hold the proximal portion and the distal portion together during normal use of the syringe, and is breakable upon application of an additional force applied to the proximal portion along a longitudinal axis of the plunger rod.

An impulse reduction system may be used to reduce or prevent the proximal portion from applying a distally directed impulse to the distal portion after the breakable connection is broken. In one embodiment, the impulse reduction system includes a projection on the proximal portion that is configured to contact the barrel after the breakable connection is broken. In another embodiment, the impulse reduction system includes a first braking surface disposed on the proximal portion, and a second braking surface disposed on the distal portion; the second braking surface is adapted to slidingly engage with the first braking surface to create a motion-resistive force between the proximal portion and the distal portion. In yet another embodiment, the impulse reduction system comprises an elastic element that is disposed within a gap along the longitudinal axis, the gap separating the proximal portion from the distal portion.

BRIEF DESCRIPTION OF THE DRAWINGS

FIG. 1A is a perspective view of a syringe in accordance with a first embodiment;

FIG. 9A is a partial perspective view of a syringe including the plunger rod shown in FIG. 8 disposed within a syringe barrel in a partially retracted position;

DETAILED DESCRIPTION

Figure 1B:
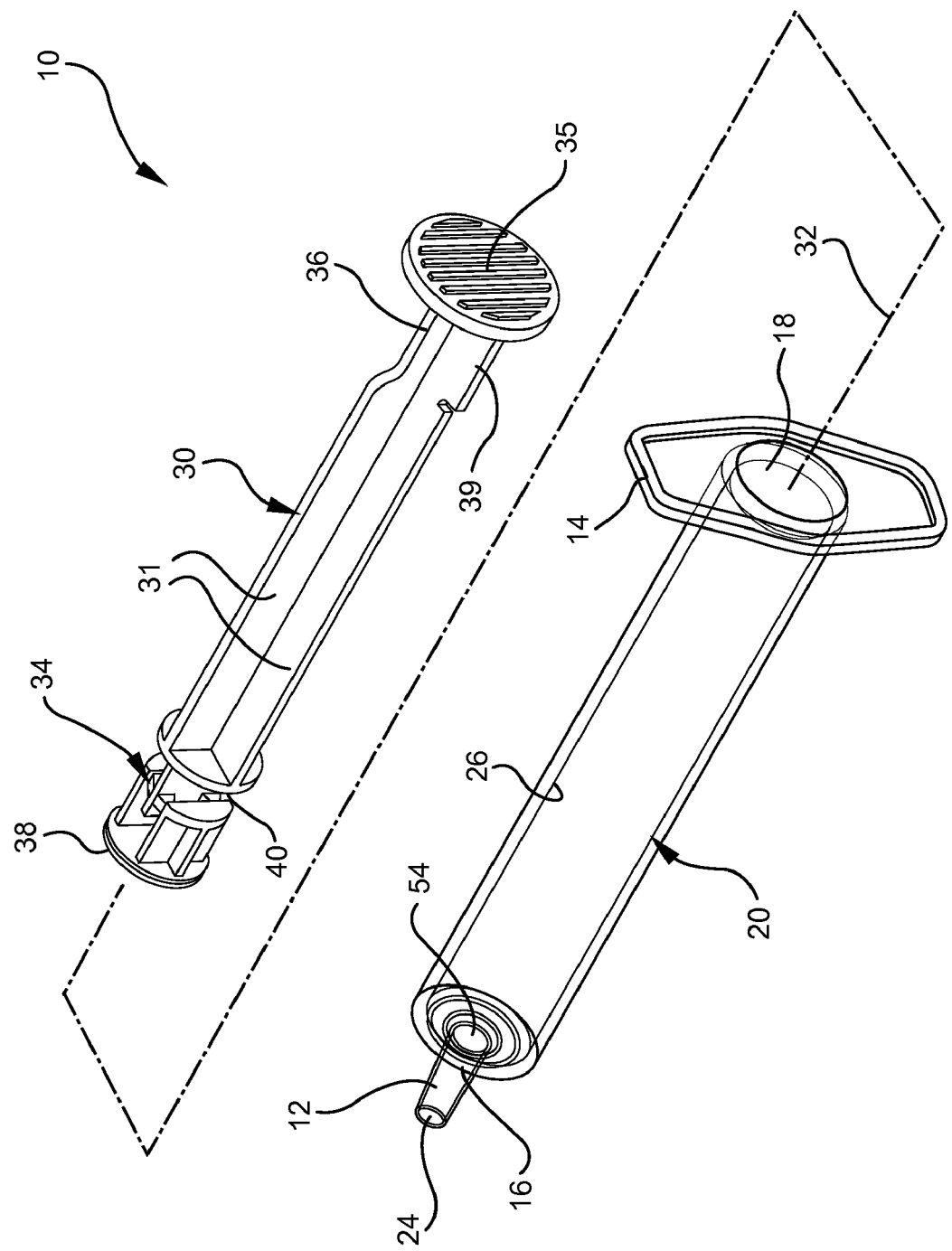
FIG. 1B is an exploded perspective view of the syringe shown in FIG. 1 depicting a barrel and a collapsible plunger rod.
Figure 2:
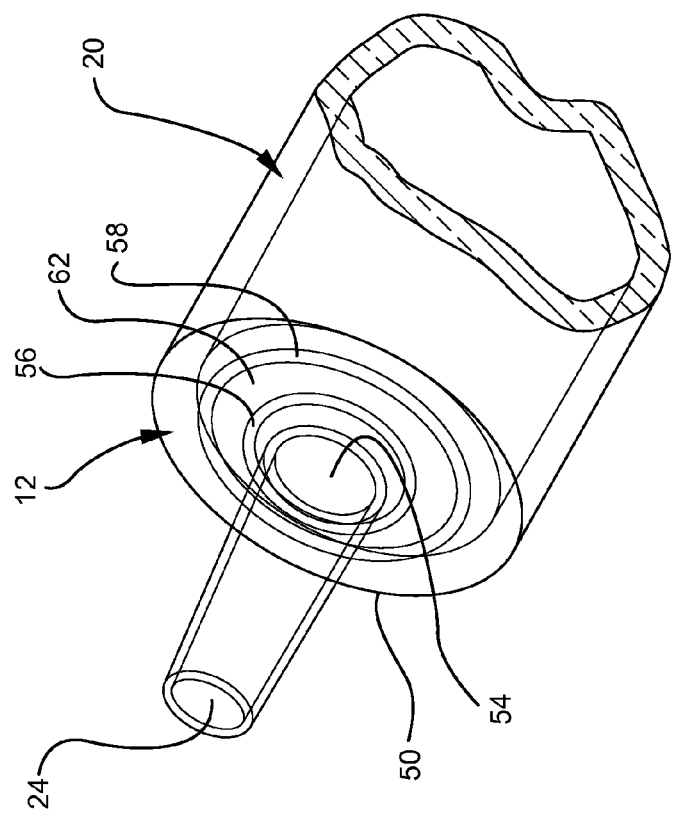
FIG. 2 is a partial perspective view of a distal portion of the syringe barrel depicted in FIG. 1.

Before describing several exemplary embodiments, it is to be understood that the invention is not limited to the details of construction set forth in the following description and drawings. The invention is capable of other embodiments and of being practiced or carried out in various ways. Additionally, a convention employed in this application is that the term "proximal" denotes a direction closest to a practitioner, while the term "distal" denotes a direction furthest from the practitioner.

According to one embodiment depicted in FIGS. 1, 2, 3, 4A and 4B, a syringe 10 includes a barrel 20 having an internal surface 26 defining a fluid chamber 18, a distal end 12, a proximal end 14, and a breakable or collapsible plunger rod 30. The plunger rod 30 can be slidably disposed within the barrel 20. The plunger rod 30 includes a distal portion 34, a proximal portion 36 and a plunger 38 connected to the distal portion 34. In the embodiment shown, the distal portion 34 and the proximal portion 36 are connected to each other via collapsible or breakable connection 40. However, it will be understood that the invention is not limited to syringes including a plunger rod including a collapsible or a breakable connection. The plunger 38 is slidably positioned in fluid-tight engagement with the internal surface 26, and is able to slide distally and proximally along longitudinal centerline 32. The distal end 12 of barrel 20 includes an elongate tip 16, which has a passageway 24 that provides fluid communication with the chamber 18. The distal end 12 also defines a roof 50, which faces the proximal end 14. The roof 50 has an opening 54 that is substantially aligned with the passageway 24, and which provides fluid communication between the passageway 24 and the chamber 18.

By moving the plunger rod 30 distally, the plunger 38 may force fluids out of passageway 24 in the elongate tip 16. By moving proximally, the plunger 38 may draw fluids through the passageway 24 and into the fluid chamber 18. It will be appreciated by those skilled in the art that the elongate tip 16 of the syringe 10 may be releasably or permanently connected to a needle assembly via a hub, as is known in the art. Such needle assemblies include, but are not limited to, Luer lock type needle assemblies and Luer slip type needle assemblies. It is further within the purview of this invention to include a needle assembly having a one-piece construction wherein the cannula and the hub are formed from a single piece.

The plunger 38 has a plunger head or plunger face 52 that faces the roof 50. The roof 50 includes a first protrusion 56 and a second protrusion 58. The first protrusion 56 extends in the proximal direction from primary roof surface 59, and provides a first ridge that forms a closed loop around the opening 54. That is, the first closed ridge formed by the first protrusion 56 is substantially concentric with the elongate tip 16, as viewed along the longitudinal axis 32. For purposes of the following disclosure, "substantially concentric" is intended to mean that one region is fully surrounded by another region, as viewed along the longitudinal axis 32, even though their respective geometric centers do not exactly correspond. Hence, as viewed along the longitudinal axis 32, the first protrusion 56 surrounds the opening 54. Similarly, the second protrusion 58 forms a second closed ridge around the first protrusion 56. In the embodiment shown, the first protrusion 56 is substantially concentric with the second protrusion 58.

It will be appreciated that the barrel 18, elongate tip 16, roof 50, protrusions 56, 58 and primary face or roof surface 59 may all be integrally formed from the same piece of material, such as molded plastic or the like. Hence, the roof 50, which includes the primary roof surface 59 and the protrusions 56, 58, may all be part of the same piece of material. However, for purposes of the present invention, it may be convenient to consider the protrusions 56, 58 as being disposed on the primary roof surface 59. That is, the primary roof surface 59 would be that surface presented by the roof 50 if the protrusions 56, 58 were not present.

Figure 3:
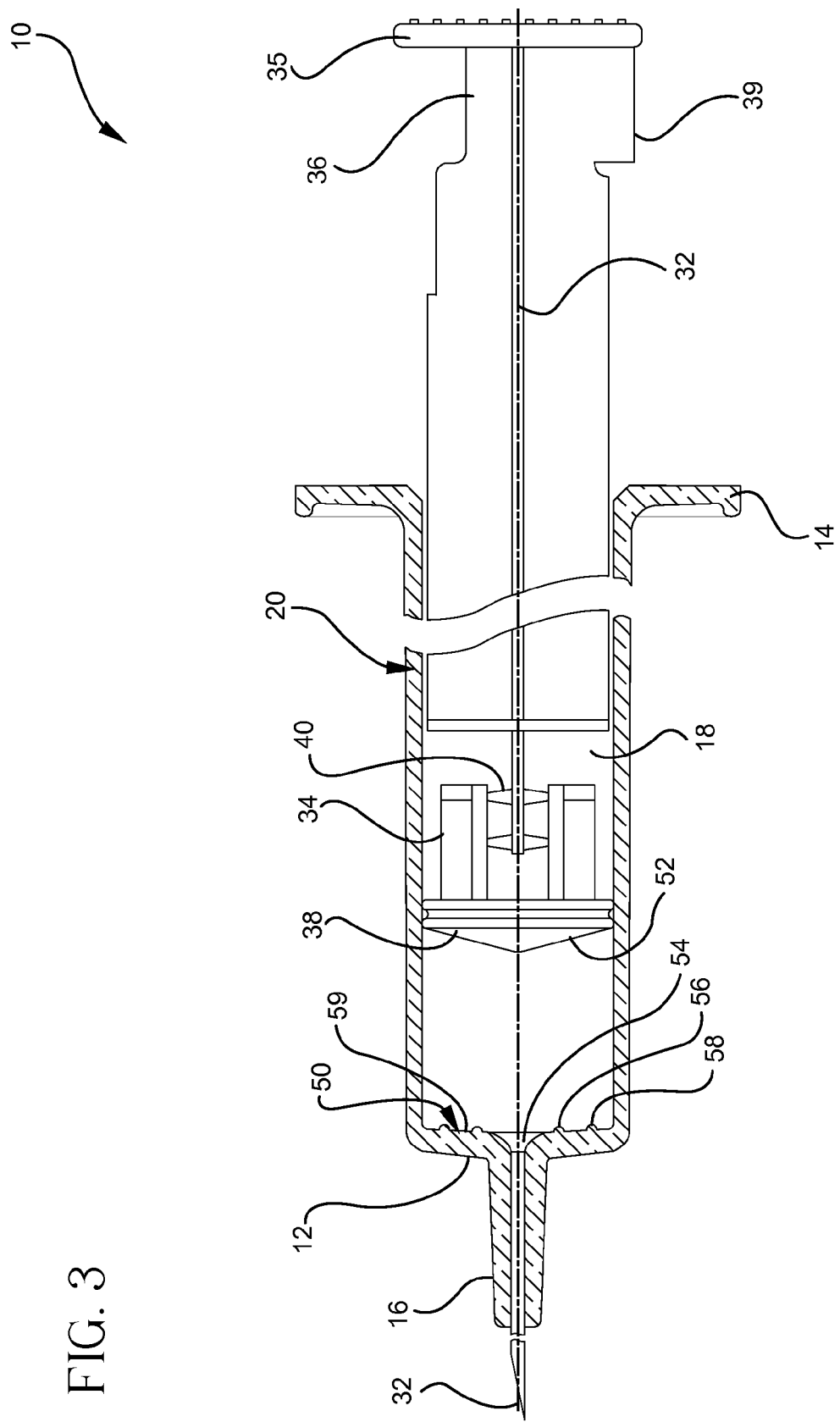
FIG. 3 is a cross-sectional view taken along line 3-3 of FIG. 1 showing the plunger rod in a partially retracted position.
Figure 4A:
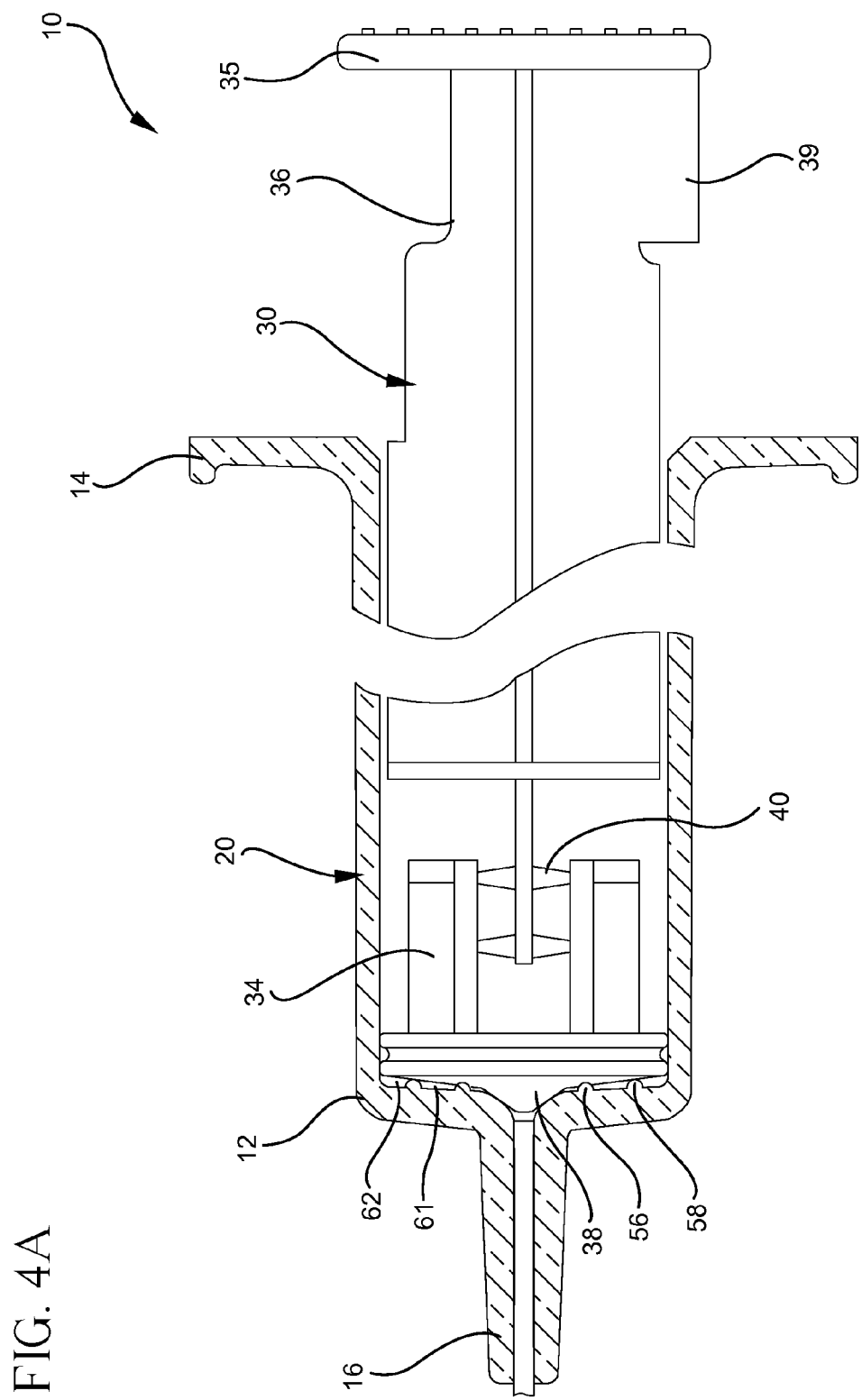
FIG. 4A shows a cross-sectional view of the syringe shown in FIG. 1 with the plunger rod distally advanced prior to collapse of the collapsible plunger rod.
Figure 4B:
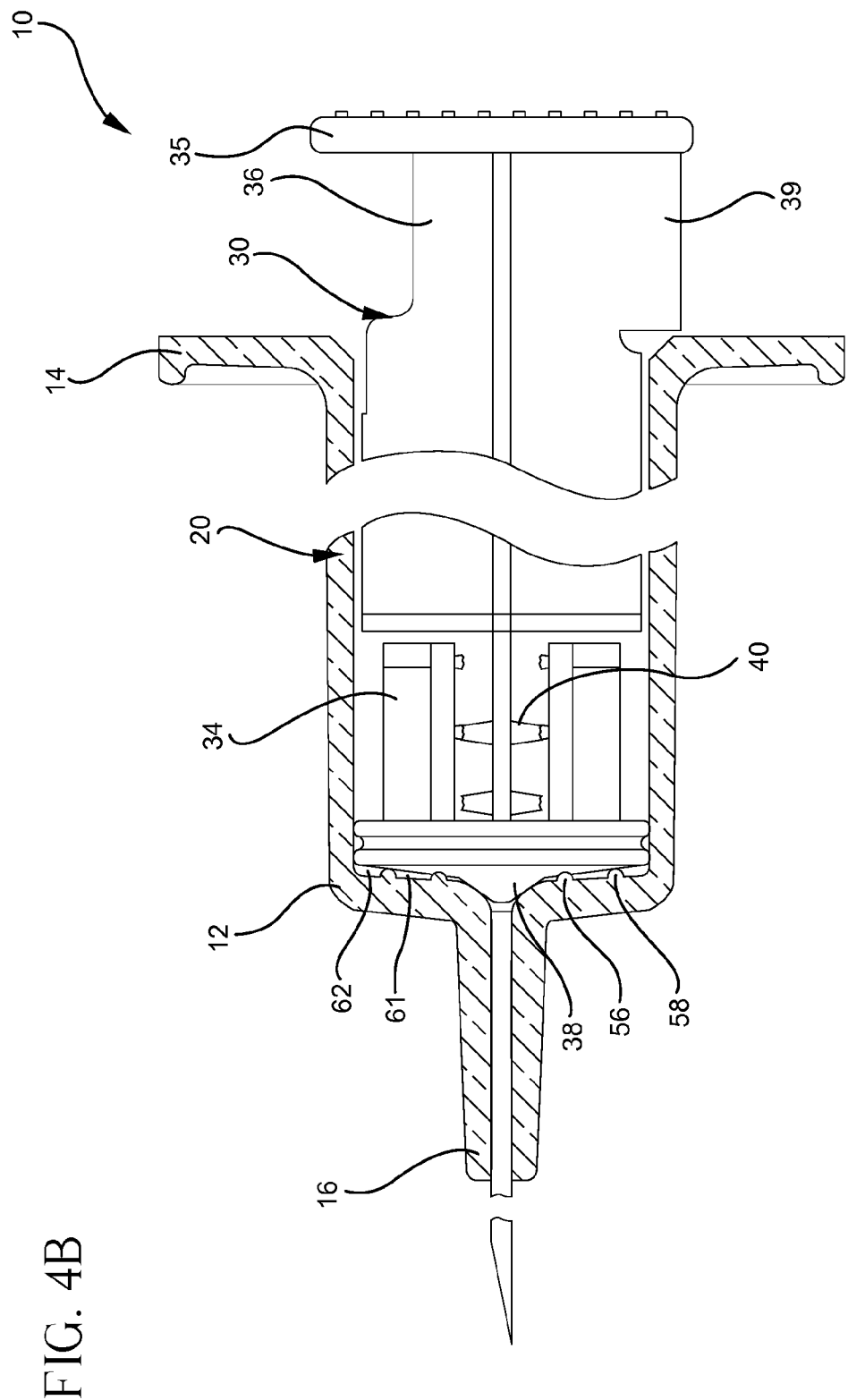
FIG. 4B shows a cross-sectional view of the syringe shown in FIG. 1 after collapse of the collapsible plunger rod.

As shown in FIGS. 3, 4A-4B, when the plunger 38 is distally extended, the plunger 38 contacts the roof 50. FIG. 3 shows the plunger in a retracted position, while FIG. 4A shows the plunger rod advanced distally prior to the breakable or collapsible plunger rod collapse or breaking. FIG. 4B shows the plunger rod after collapse or breakage of the plunger rod. In particular, the plunger head 52 contacts the first protrusion 56 and the second protrusion 58. The plunger head 52 may not, however, contact the primary roof surface 59. The first protrusion 56 and second protrusion 58 thus may prevent face-to-face contact between the plunger head 52 and the primary roof surface 59. However, the first protrusion 56 and the second protrusion 58 do create a fluid-tight seal with the plunger head 52. Of course, the plunger head 52 also forms a fluid-tight seal with the internal surface 26 of the fluid chamber 18. As a result, it will be appreciated that a first reservoir or channel 62 is thereby formed between the first protrusion 56, the second protrusion 58 and the gap between the plunger head 52 and primary roof surface 59. This first channel 62 is adapted to isolate fluid from the opening 54, and hence from the passageway 24; that is, the first channel 62 is not in fluid communication with the passageway 24. In other words, the fluid in channel 62 is substantially isolated from the passageway 24. It is therefore unlikely for any fluid within the first channel 62 to spray from the elongate tip 16. Similarly, a second channel 64 is formed between the second protrusion 58 and the internal surface 26, which is also isolated from the passageway 24. Any fluid trapped in second channel 64 is substantially isolated from the passageway 24 and from spraying from the tip 16.

As shown in FIGS. 3 and 4A, steady application of distal pressure upon flange 35 on the proximal end 36 of plunger rod 30 causes the plunger rod 30 to move forward distally. Breakable connection 40 is designed to withstand standard-use pressures applied during delivery of medication from the syringe. Fluid within fluid chamber 18 is thus expelled out of the elongate tip 16. Eventually, the plunger head 52 contacts the roof 50, which marks the most distal extension of the plunger rod 30 with respect to the barrel 20. When the plunger rod is extended distally, the first protrusion and second protrusion form the first channel 62 and second channel 64, and fluid contained in these channels are isolated from the passageway 24. The user then applies an excess amount of pressure upon the flange 35, which causes the breakable connection 40 to shear, thus activating the breakable connection 40 and disabling the plunger rod 30. The proximal portion 36 of the plunger rod 30 is thus mechanically disengaged from the distal portion 34 of the plunger rod 30. Because of the force incident on the flange 35 at the time of failure of the breakable connection 40, the proximal portion 36 will tend to rapidly advance towards the distal portion 34. Should the proximal portion 36 strike the distal portion 34, an impulse will be generated; as the distal portion 34 comprises the plunger 38, this impulse is imparted to the plunger 38, and hence to the plunger head 52.

Even though in the embodiment shown, the first protrusion 56 and second protrusion 58 are designed to form channels or reservoirs to mitigate any spraying of fluid caused by such an impulse upon the plunger 38, in certain embodiments, it may be desirable to provide an impulse-reduction system to reduce, or prevent, such impulses. As shown in FIG. 4B, an impulse reduction system may be provided by having a projection 39 on the proximal end 36 of plunger rod 30 that contacts the barrel 20 after the breakable connection 40 fails, but before the proximal end 36 can strike the distal end 34. This projection 39 may be formed by one or more of the fins 31 that may form the proximal portion 36.

Figure 4C:
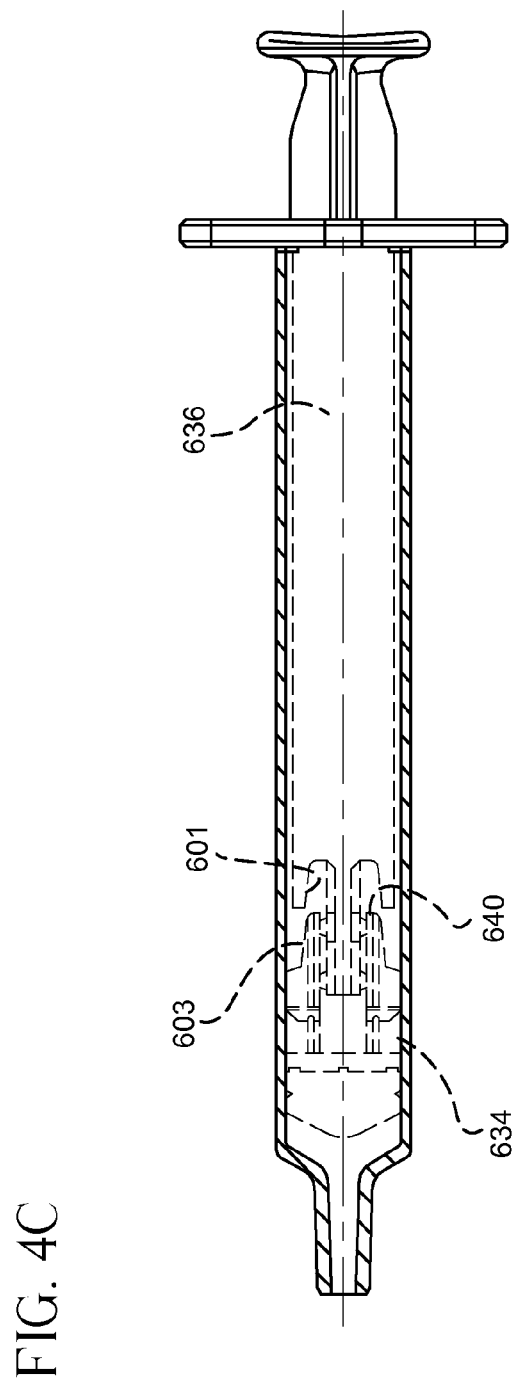
FIG. 4C shows a cross-sectional view illustrating a plunger including a collapsible plunger rod according to another embodiment disposed within a syringe barrel in a partially retracted position.
Figure 4D:
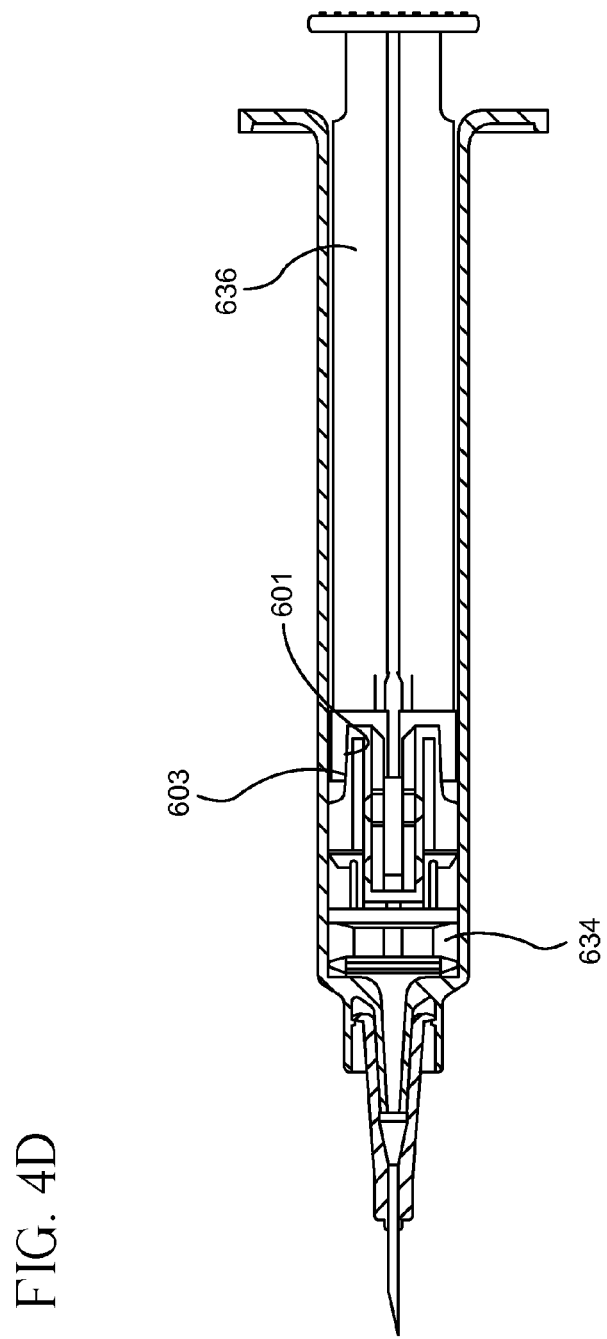
FIG. 4D shows a cross-sectional view of the syringe shown in FIG. 4C, with the plunger rod distally advanced into the syringe barrel.

An alternative impulse reduction system is depicted in FIGS. 4C and 4D. The impulse reduction system comprises a first breaking surface 601 on the proximal portion 636 of plunger rod 630, and a corresponding second breaking surface 603 on the distal portion 634 of the plunger rod 630. When breakable connection 640 shears under excessive force, the proximal portion 636 advances towards the distal portion 634. As a result, the first breaking surface 601 comes into contact with, and rubs against, the second breaking surface 603. This, through friction, creates a motion-resistive force between the proximal portion 636 and the distal portion 634, which slows the relative speed between the proximal portion 636 and the distal portion 634, and which thus reduces the impulse imparted onto the distal portion 634 by the proximal portion 636.

Figure 5:
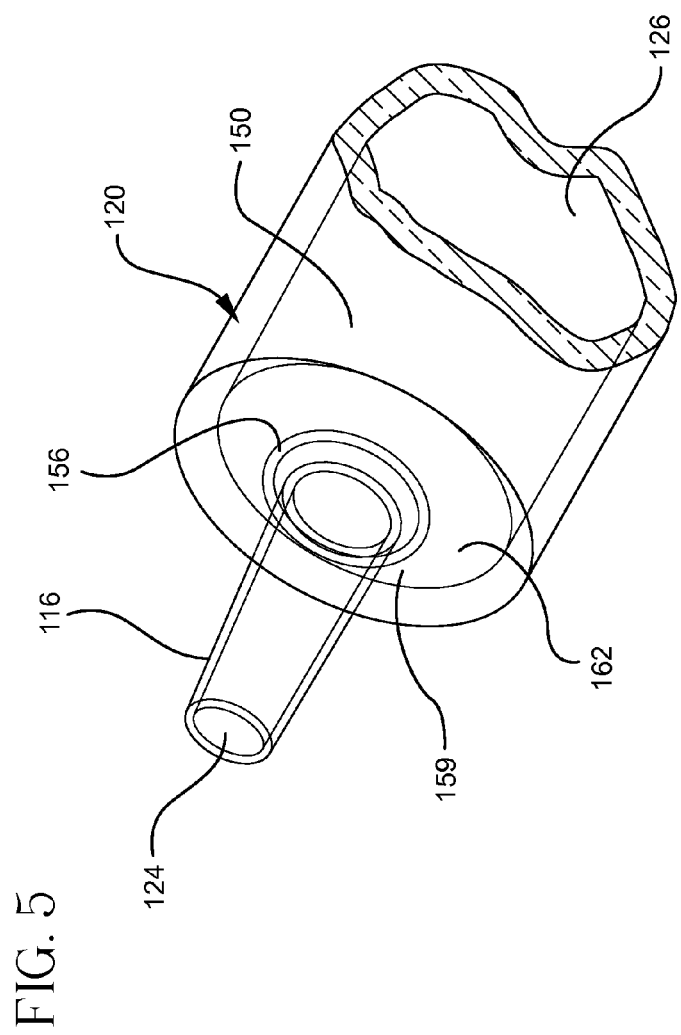
FIG. 5 is a partial perspective view of a distal portion of a syringe barrel according to another embodiment.

Although two or more protrusions may be desirable so as to prevent tilting of the plunger, it is possible to provide only a single protrusion, and this is shown in FIG. 5. A single ridge 156 extends in the proximal direction from roof 150 of barrel 120. This protrusion 156 forms a closed ridge that is concentric with passageway 124 of elongate tip 116. When the plunger head contacts the roof 150, a channel 162 is formed between the plunger head, primary roof surface 159, protrusion 156 and internal surface 126 of barrel 120. The channel 162 is isolated from passageway 124, and hence fluid trapped within the channel 162 is prevented from spraying from the elongate tip 116.

Figure 6:
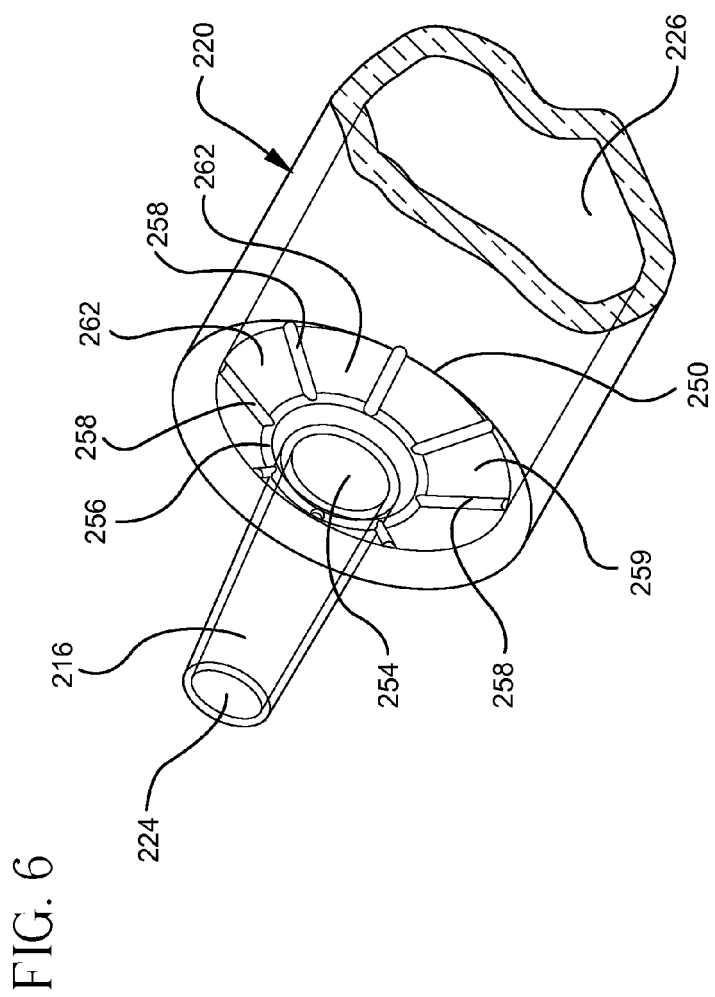
FIG. 6 is a partial perspective view of a distal portion of a syringe barrel according to another embodiment.

As shown in FIG. 6, the protrusion may not only be circular in form, but may also extend along a radial direction. Barrel 220 includes a roof 250, with an elongate tip 216 extending therefrom. A first protrusion 256 extends proximally from the primary roof surface 259, and forms a closed, circular ridge that is concentric with, and adjacent to, opening 254; hence the first protrusion 256 is also concentric with elongate tip 216. A plurality of second protrusions 258 extend radially from the first protrusion 256 towards the internal surface 226 of the barrel 220. When the plunger contacts the roof 250, a plurality of channels 262 are formed that are sealed off from the opening 254, and hence from passageway 224 of elongate tip 216.

Figure 7A:
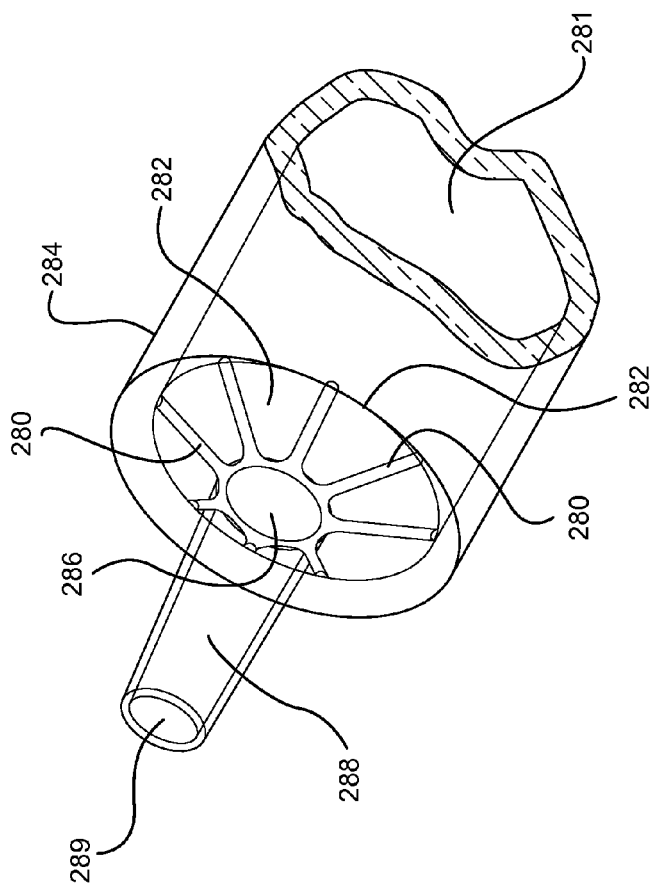
FIG. 7A is a partial perspective view of a distal portion of a syringe barrel according to still another embodiment.
Figure 7B:
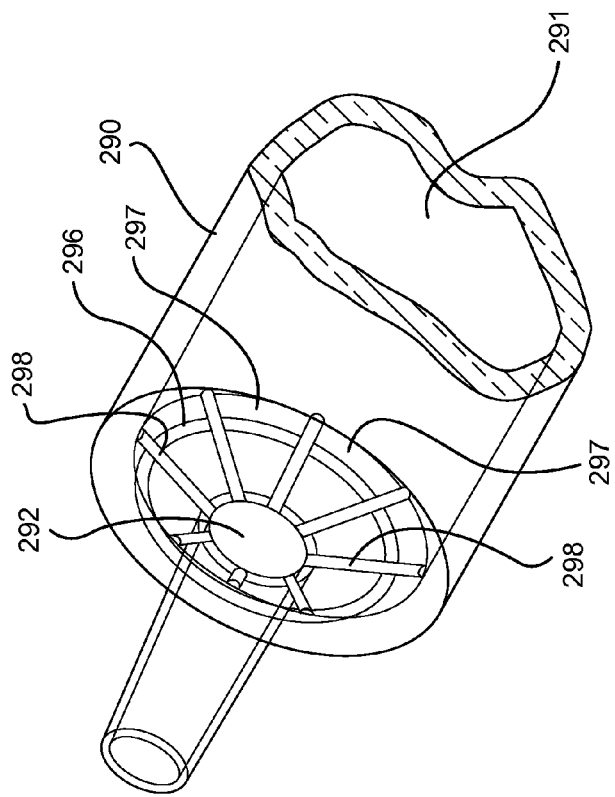
FIG. 7B is a partial perspective view of a distal portion of a syringe barrel according to another embodiment.

FIGS. 7A and 7B illustrate variations of the embodiment depicted in FIG. 6. As shown in FIG. 7A, it is possible to have only radially extending protrusions 280 on the roof 282 of barrel 284. The roof 282 may have an opening 286 for elongate tip 288 and passageway 289, and the protrusions 280 may extend along the radial direction from the opening 286 towards the internal surface 281 of barrel 284. As shown in FIG. 7B, the ring-shaped first protrusion 296 may be formed adjacent to the internal surface 291 of the barrel 290, and radially extending second protrusions 298 may run from the opening 292 towards the internal surface 291.

Figure 8:
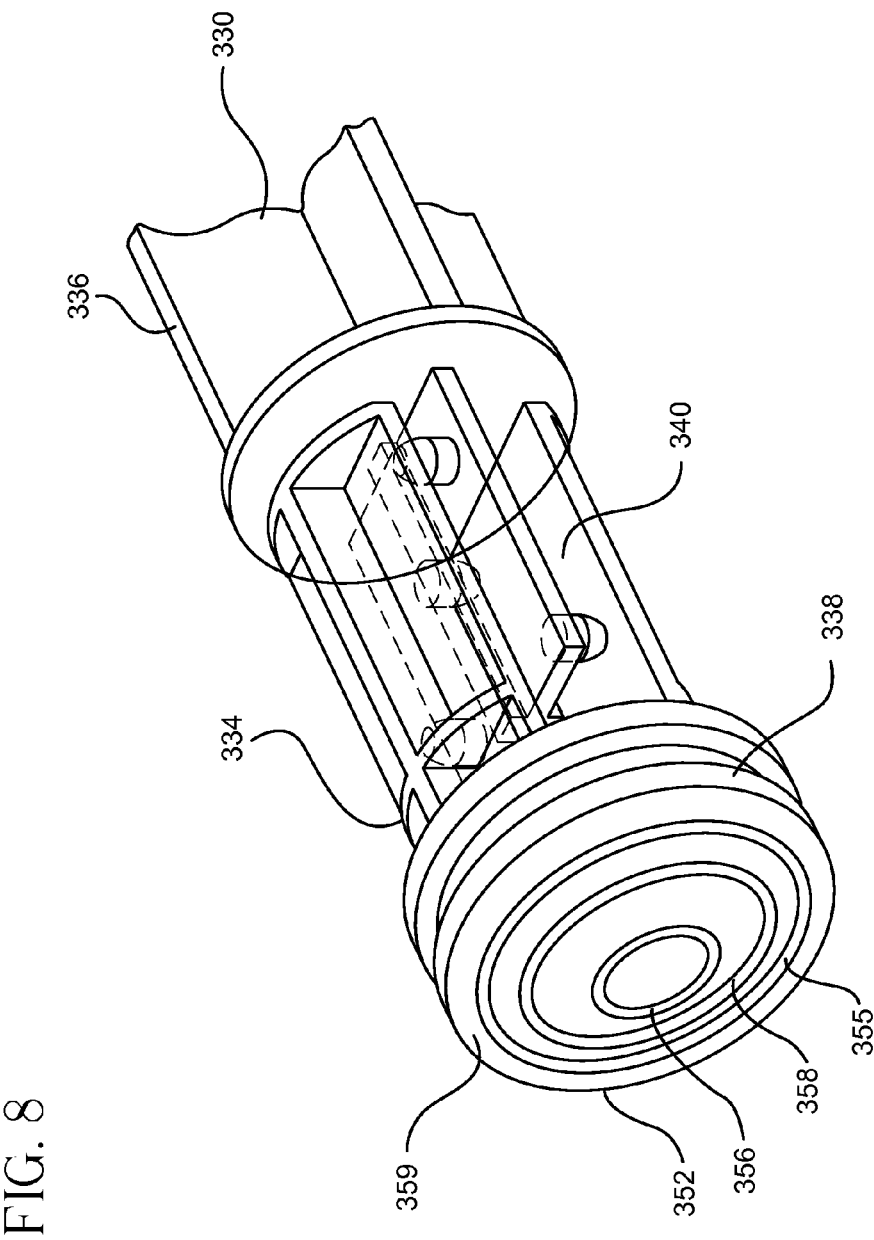
FIG. 8 is a partial perspective view of a plunger rod according to another embodiment.

It is possible to dispose the protrusions on the plunger head surface instead of the primary roof surface. An example of this is depicted in FIG. 8, in which a plunger rod, an in the embodiment shown, a collapsible plunger rod 330 comprises a proximal portion 336 connected to distal portion 334 with a breakable connection 340. A plunger 338 is attached to the distal end of distal portion 334. The most distal portion of the plunger 338 includes the plunger head 252. The plunger head 352 has a plunger head face or plunger head surface 359, and extending distally from the plunger head surface 359 are a first protrusion 356, a second protrusion 358 and a third protrusion 355. The plunger 338 may be integrally made from a single molded body, and may be a traditional, non-collapsible type plunger rod.

Figure 9B:
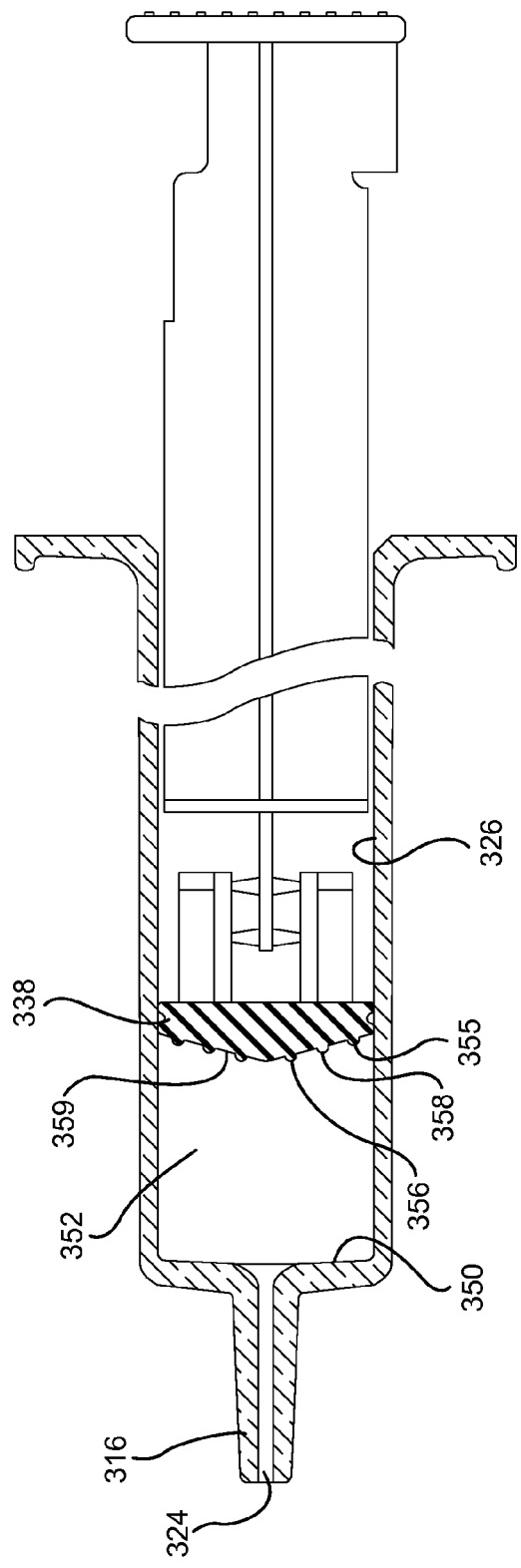
FIG. 9B is a cross sectional view taken along line 9B-9B of FIG. 9A.
Figure 9C:
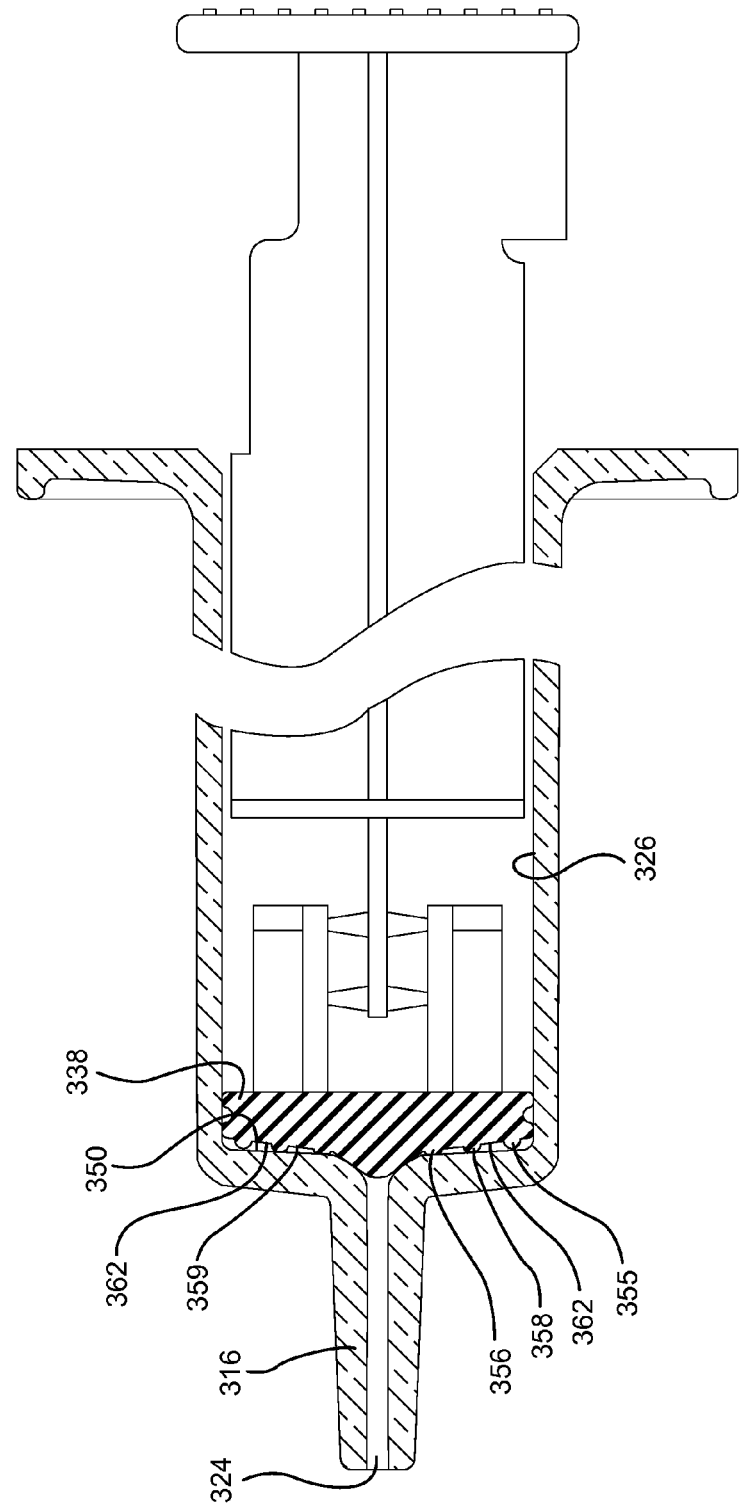
FIG. 9C is a cross-sectional view of the syringe shown FIG. 9B with the plunger rod shown in a distally advanced position.

As shown in FIG. 9A, 9B and 9C, as the plunger 338 is advanced distally, the plunger head 352 contacts the roof 350. In particular, the protrusions 355, 356 and 358 contact the roof 350, whereas the plunger head surface 359 does not. That is, the protrusions 355, 356 and 358 may prevent face-to-face contact between the plunger head surface 359 and the primary roof surface. As a result, channels 362 are formed that trap fluid and isolate the fluid from the passageway 324 of elongate tip 316. The first protrusion 356 may form a closed ridge that is adjacent to, and concentric with, elongate tip 316. The second protrusion 358 may be concentric with the first protrusion 356, and the third protrusion 355 may be concentric with the first and second protrusions 356, 358, and be adjacent to internal surface 326 of barrel 320. It will be appreciated that various configurations of protrusions may be formed on the plunger head, similar to those described above with respect to the protrusions formed on the roof surface.

Figure 10:
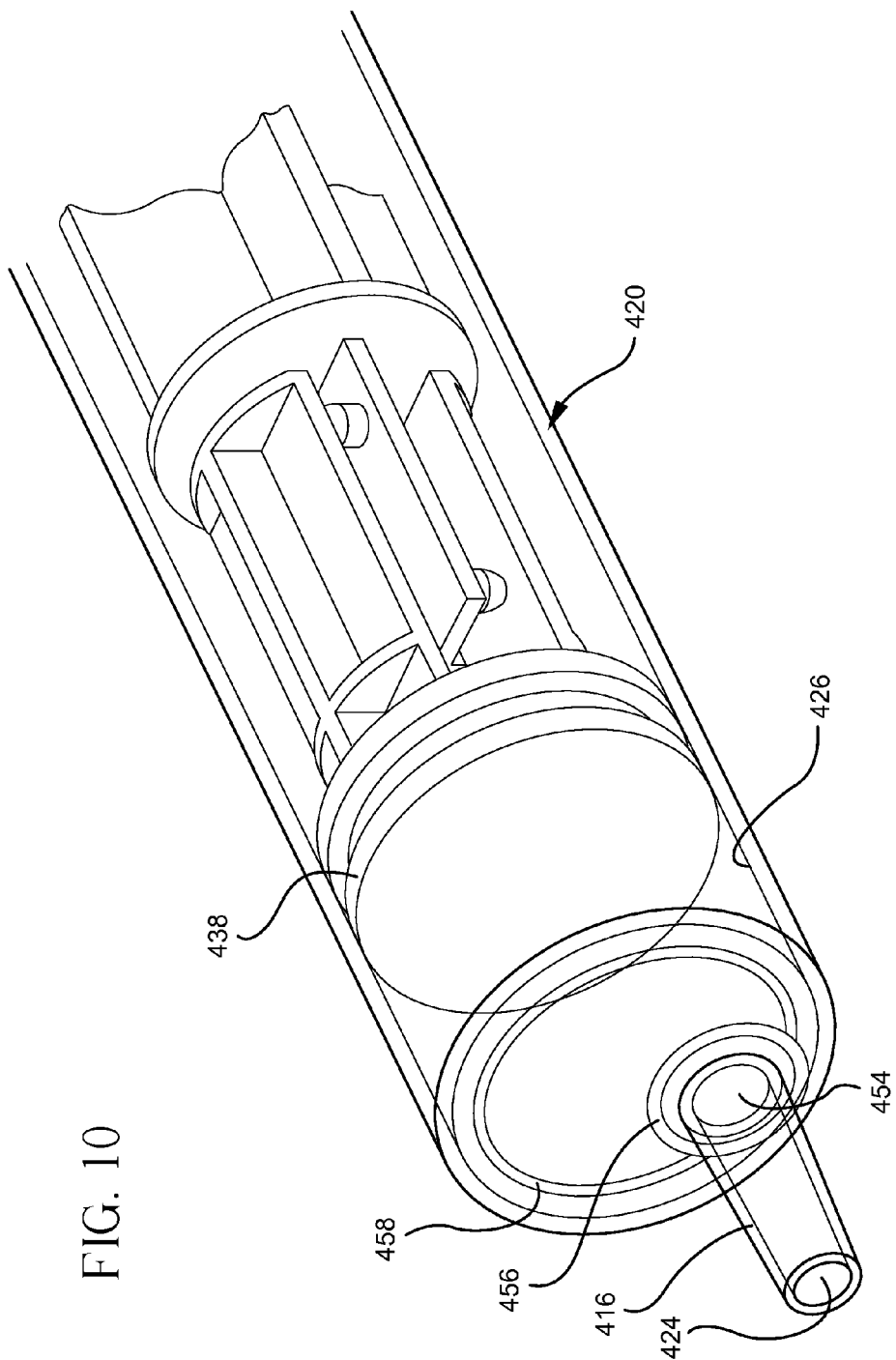
FIG. 10 is a perspective view of a syringe according to another embodiment, showing the plunger rod in a partially retracted position.
Figure 11A:
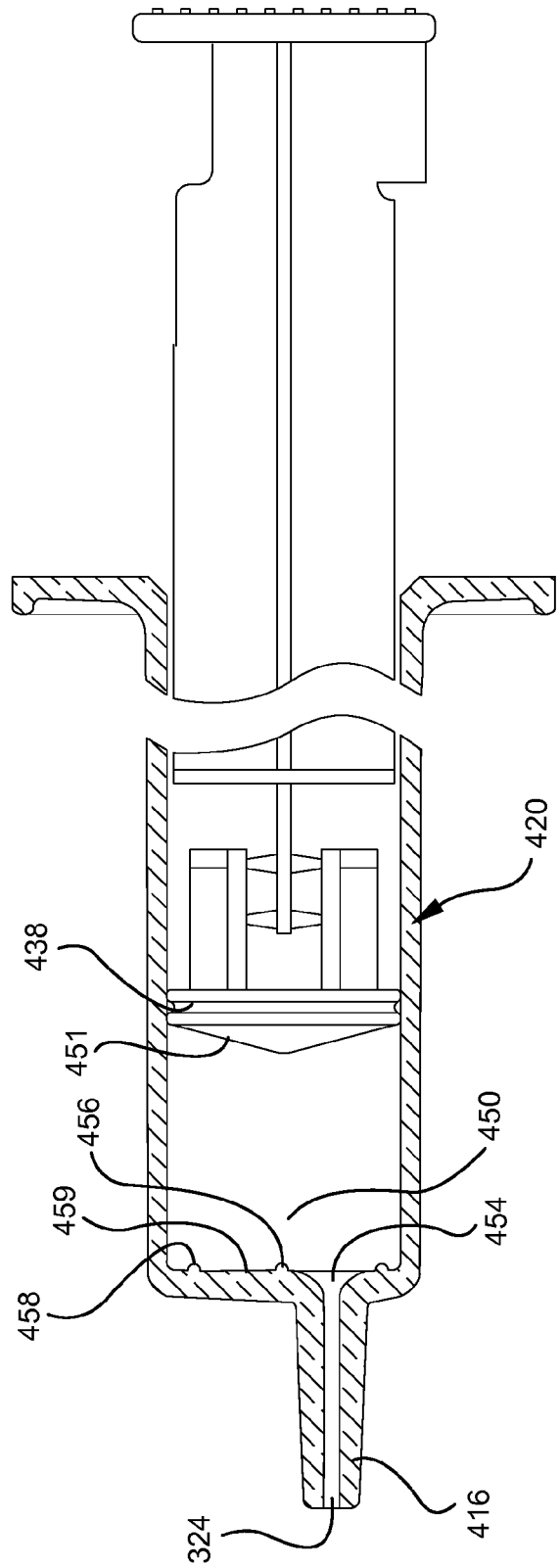
FIG. 11A is a cross-sectional view taken along line 11A-11A of FIG. 10.
Figure 11B:
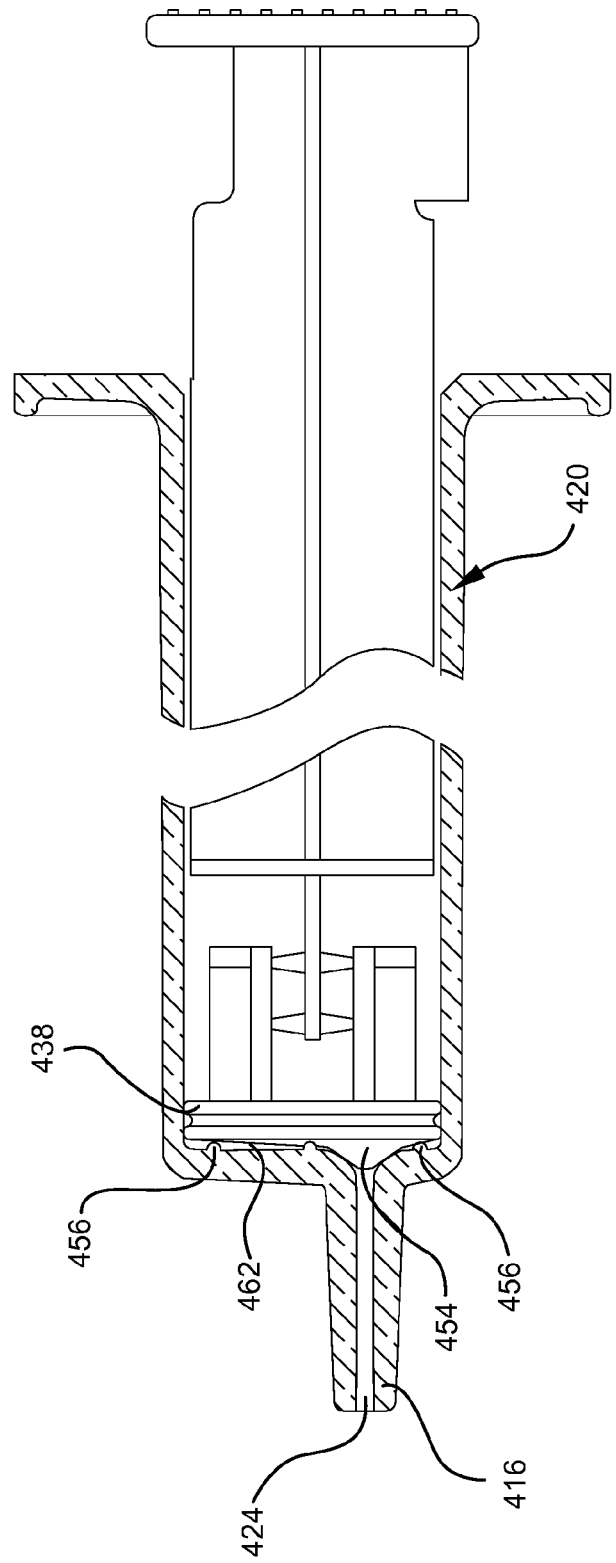
FIG. 11B is a cross-sectional view of the syringe shown in FIG. 10 with the plunger rod in a distally advanced position.

It is not necessary that closed loop protrusions, formed either on the primary roof surface or on the plunger head surface, be substantially concentric with each other. As shown in FIG. 10, a first protrusion 456 on primary roof surface 459, concentric with, and adjacent to, opening 454 of elongate tip 416, may intercept a second protrusion 458 that forms a closed ridge adjacent to internal surface 426 of barrel 420. As shown in FIG. 11A and 11B, as the plunger 438 advances in the distal direction, the plunger head 452 comes into contact with the roof 450 of barrel 420. Protrusions 456 and 458 prevent the plunger head surface 451 from contacting the primary roof surface 459. At contact, channels 462 are formed that are isolated from opening 454 and hence isolated from passageway 424 of elongate tip 416. FIGS. 10, 11A and 11B depict a design in which the elongate tip 416 is off-center or eccentric with respect to the roof surface 459.

Figure 12:
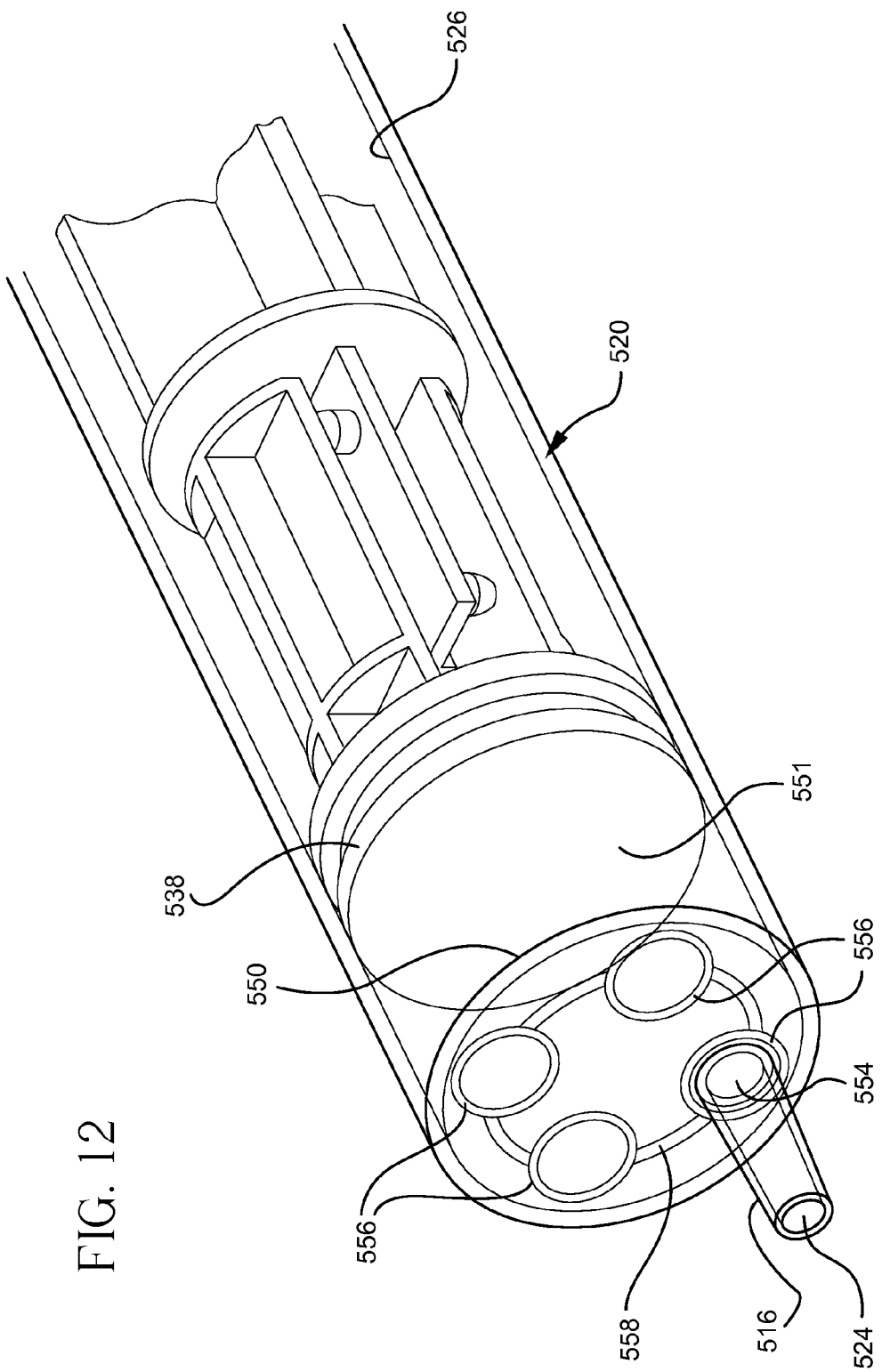
FIG. 12 is a perspective view of a syringe according to still another embodiment.

FIG. 12 presents a variation of the embodiment described above in relation to FIG. 10. As shown in FIG. 12, it is possible to have a plurality of closed-loop protrusions 556, which are intersected by another closed-loop protrusion 558. The protrusion 558 may be adjacent to the internal surface 526 of barrel 520. One of the first closed-loop protrusions 556 may be concentric with, and adjacent to, elongate tip 516 and opening 554. The other closed-loop protrusions 556 may be spaced around the length of the protrusion 558 to provide stability to plunger 538 when plunger face 551 contacts roof 550. When the plunger is distally advanced, channels or reservoirs (not shown) are formed between the protrusions and the plunger face 551 that trap fluid and prevent the fluid from being sprayed from opening 524 in distal tip 516.

Although the invention herein has been described with reference to particular embodiments, it is to be understood that these embodiments are merely illustrative of the principles and applications of the present invention. For example, other variants of protrusions formed on either one or both of the plunger head or roof of the barrel may be provided. In other words, the protrusions do not necessarily have to be in the form of substantially concentric rings and/or radially-extending protrusions. The protrusions should be capable of forming a channel or reservoir from isolating fluid from the passageway formed at the distal tip of the syringe. In addition, protrusions may be formed on both the plunger head and on the roof surface in the same syringe to provide greater isolation of the facing surfaces of the roof surface and the plunger face. It is therefore to be understood that numerous modifications may be made to the illustrative embodiments and that other arrangements may be devised without departing from the spirit and scope of the present invention as defined by the appended claims.

The invention claimed is:

1. A syringe comprising:
 a barrel including a fluid chamber, a proximal end, a distal end defining a roof facing said proximal end, said roof including an opening therethrough, and an elongate tip extending from said distal end including a passageway therethrough in fluid communication with said chamber and said opening;
 a plunger slidably disposed within said barrel, said plunger including a plunger head that faces said roof, said plunger head being cone shaped with a tip that protrudes into the opening when said plunger head contacts said roof; and
 a first protrusion and a second protrusion disposed on said roof, said first protrusion adapted to form a first channel between said plunger head and said roof by contacting said plunger head without contacting any ridge on said plunger head and said second protrusion adapted to form a second channel between said plunger head and said roof by contacting said plunger head without contacting any ridge on said plunger head when said plunger is distally extended, said first and second channels adapted to isolate fluid from said passageway, said plunger head not contacting said roof.

2. The syringe of claim 1, wherein said first protrusion forms a first closed ridge substantially concentric with said elongate tip.

3. The syringe of claim 2, wherein said first closed ridge is adjacent to said opening.

4. The syringe of claim 2, wherein the second protrusion forms a second closed ridge substantially concentric with said first closed ridge.

5. The syringe of claim 1, wherein said first protrusion is integrally formed with said roof.

6. The syringe of claim 1, further comprising:
 a plunger rod including a longitudinal axis, a proximal portion and a distal portion connected by a breakable connection, said distal portion including said plunger positioned in fluid-tight engagement with an inside surface of said chamber for drawing fluid into and out of said chamber by movement of said plunger relative to said barrel, said breakable connection being strong enough to hold said proximal portion and said distal portion together during normal use of said syringe and breakable upon application of an additional force applied to said proximal portion along said longitudinal axis.

7. The syringe of claim 6, further comprising an impulse reduction mechanism for inhibiting said proximal portion from applying a distally directed impulse to said distal portion after said breakable connection is broken.

8. The syringe of claim 6, wherein said impulse reduction mechanism includes a projection on said proximal portion configured to contact said barrel after said breakable connection is broken.

9. The syringe of claim 8, wherein said proximal portion includes a plurality of outwardly projecting ribs and said projection is on at least one of said ribs.

10. The syringe of claim 9, wherein said projection is integrally formed with said rib.

11. A method of reducing fluid spray from the distal end of a syringe including a barrel with a fluid chamber having fluid therein, a proximal end, a distal end defining roof facing said proximal end, said roof including an opening therethrough, and an elongate tip extending from said distal end including a passageway therethrough in fluid communication with the opening and the chamber and a plunger slidably disposed within said barrel, said plunger including a plunger head that faces said roof, said plunger head being cone shaped and having a tip that extends into said opening when said plunger head contacts said roof, the method comprising disposing a first ridge and a second ridge concentrically around the passageway between said plunger head and said roof surface to form a first channel and a second channel adapted to isolate fluid from the opening and the passageway when the plunger rod is distally advanced within the barrel, wherein neither the first ridge nor the second ridge contact a ridge in the cone shaped plunger head.

* * * * *